Figure 1:
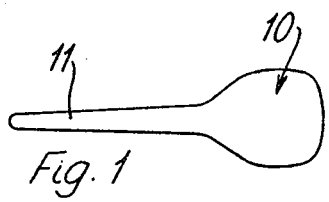
Figure 3:
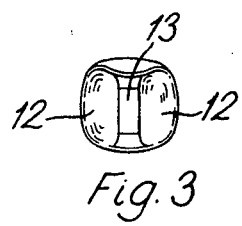

United States Patent [19]
Bentley et al.

[11] 3,946,445
[45] Mar. 30, 1976

[54] ENDOPROSTHETIC BONE JOINT

[75] Inventors: George Bentley, Bladon; Graham Deane, Chesterton, both of England

[73] Assignee: National Research Development Corporation, London, England

[22] Filed: Apr. 30, 1975

[21] Appl. No.: 573,155

[30] Foreign Application Priority Data
May 3, 1974 United Kingdom............... 19558/74

[52] U.S. Cl................................. 3/1.91; 128/92 C
[51] Int. Cl.²............................................ A61F 1/24
[58] Field of Search............................ 3/1.9–1.913, 3/1; 128/92 C, 92 CA

[56] References Cited
UNITED STATES PATENTS

| | | |
|---|---|---|
| 3,506,982 | 4/1970 | Steffee .................................... 3/1.91 |
| 3,651,521 | 3/1972 | Devas ..................................... 3/1.91 |
| 3,760,427 | 9/1973 | Schultz ................................... 3/1.91 |
| 3,805,302 | 4/1974 | Mathys ................................... 3/1.91 |
| 3,869,729 | 3/1975 | Attenborough............................. 3/1 |

*Primary Examiner*—Ronald L. Frinks
*Attorney, Agent, or Firm*—Cushman, Darby & Cushman

[57] ABSTRACT

An endoprosthetic replacement for the metacarpophalangeal joint has two components, each with a rounded bearing body and integrally projecting intramedullary stem. The metacarpal component body provides two concave grooves separated by a concave rib, and the phalangeal component body provides two convex ribs and a convex groove, these ribs and grooves intermeshing for component engagement. The concave and convex configurations respectively subtend angles less and greater than 180° to allow longitudinal sliding, and the convex groove widens towards one end to allow lateral rocking. The stems lie in the planes of their grooves and ribs, but are respectively inclined and parallel to the arcuate bisectors of such configurations. This allows the central rib and groove to limit the sliding abutment at their ends, with the stems parallel at one limit and angled at the other. The metacarpal component body overhangs its concave rib end further from its stem to provide, with the rounded bodies, knuckle simulation, and the convex groove is widened at the corresponding end.

7 Claims, 8 Drawing Figures

U.S. Patent    March 30, 1976    3,946,445

ENDOPROSTHETIC BONE JOINT

This invention concerns prostethic devices and more particularly endoprosthetic bone joint devices.

The invention has in fact been developed in respect of the metacarpophalangeal joint and will be described with reference to the same. However, the invention may be suitable for application to other joints, particularly the interphalangeal, toe, and elbow joints.

Various proposals have been made for endoprosthetic bone joint devices, and some of these proposals have been followed by commercial production and clinical use. However, those of the latter proposals which have been directed to use in fingers are not without disadvantage. Much of this disadvantage stems from providing a device of a mechanically constrained form which inherently provides only a part of the articulation capability which normally is present in the natural joint to be replaced. For example: use has been made of mechanically-linked hinges which allow only pivotal rotation about a single axis and in a single planar direction perpendicular to that axis, but such hinges are inappropriate for application to the metacarpophalangeal joint which has both flexion-extension and abduction-adduction capability and such hinges are, in any case, disadvantageous in the resultant transmission therethrough of forces which tend to weaken the hinge fixation to the relevant bones. Disadvantage also arises in such hinges from a previously common objective of close fits between mutually articulatory component parts, which objective leads to difficulty in manufacture and often a reduced range of flexion compared to the natural joint. Other previously proposed finger joint devices are in the form of a single component and these suffer the disadvantage of requiring undue effort to flex the same.

The present invention derives from the initial consideration that the articulation capabilities of bone joints are not determined by the geometry of the relevant bone surfaces alone but also, to a large extent, by the structure of the joint capsule and related ligaments. As a second consideration, account is to be taken of the fact that provision of an endoprosthetic bone joint device is most common to relieve the effects of arthritic conditions, when the natural capsule will often not be fully normal and, in practice, is usually slightly stretched. A related consideration is that the surgery necessary to implantation of the device cannot be guaranteed to restore the full function of a normal capsule.

With these considerations in mind, it seems appropriate to provide a device which is of an indirectly-linked, multi-component form to be held in articulating relation by the natural capsule, and being geometrically constrained to limit the range of articulatory movement between the components without unduly constraining the freedom to move within that range.

To this end the present invention provides an endoprosthetic bone joint device comprising: a first component having a bearing surface defined by two similar, generally parallel, longitudinally concave, arcuate grooves laterally separated by a longitudinally concave, arcuate rib; and a second component having a bearing surface defined by two similar, generally parallel, longitudinally convex, arcuate ribs laterally separated by a longitudinally convex arcuate groove; said concave grooves and rib subtending angles not greater than 180°, the arcuate lengths of said convex ribs and groove exceeding those of said concave grooves and rib, and the cross-sectional dimensions and profiles of said grooves and ribs being such that said concave grooves and rib and said convex groove and ribs are respectively engageable for mutual articulation by sliding between said grooves and ribs in the longitudinal direction thereof over an angular range of greater extent and, for at least part of said range, by rocking therebetween in the transverse direction thereof over an angular range of lesser extent.

It is, of course, appropriate that the components of the proposed device be respectively adapted remotely from their bearing surfaces for securement to the bones of the relevant joint. It is presently preferred that this adaptation be effected by the provision of a respective intramedullary stem projecting integrally from the 'rear' of a bearing part in which the associated bearing surface is formed, such stem being intended for securement in association with acrylic cement or other gap-filling medium.

For a fuller understanding of the present invention, the same will now be described, by way of example, with reference to the accompanying drawings, in which:

FIGS. 1 to 4 diagrammatically illustrate the first component of one embodiment of the invention in respective plan, side, end and part cross-sectional views, and FIGS. 5 to 8 similarly illustrate the associated second component of the same embodiment.

The illustrated first component comprises a bearing part in the form of a rounded body 10 from which an elongate member 11, of smaller cross-sectional dimensions than the body 10, extends. The body 10 is relieved remotely from the member 11 to define a bearing surface comprising two similar, generally parallel, grooves 12 laterally separated by a rib 13.

Figure 2:
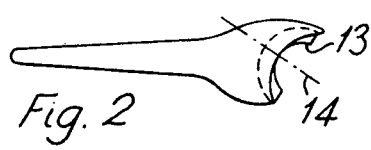

As shown in FIG. 2, each of the grooves 12 and the rib 13 is of longitudinally concave arcuate form with the direction of the bisector 14 of this arcuate form being inclined relative to the longitudinal direction of the member 11. Also, as shown in FIG. 2, the rib 13 extends longitudinally in the direction from the member 11 to the bisector 14 to a lesser distance than the adjacent part of the body 10 so that the latter overhangs the relevant end of the rib. FIG. 2 also shows the radial depth of the rib 13 to be more uniform than that of the outermost side wall portions of the grooves 12, these portions becoming progressively shallower towards their longitudinal ends.

Figure 4:
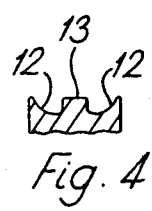

The section of FIG. 4 is taken generally in a plane of the member 11 to show the transverse profile of the grooves 12 and rib 13. In this connection it will be seen that the rib 13 is more rectangular than the grooves 12 in so far as the former has relatively flat sides whereas the latter have curved base and transversely outermost side wall portions. There are, however, no sharp corners in this profile.

The illustrated second component comprises a bearing part in the form of a rounded body 20 from which an elongate member 21 of smaller cross-sectional dimensions than the body 20, extends. The body 20 is relieved remotely from the member 21 by the provision of a groove 22 whereby the adjacent parts of the body 20 form two generally parallel ribs 23 laterally bounding the groove. Each of the groove 22 and ribs 23 is of longitudinally convex arcuate form with the bisector direction of this form being generally parallel with the longitudinal direction of the member 21.

Figure 5:
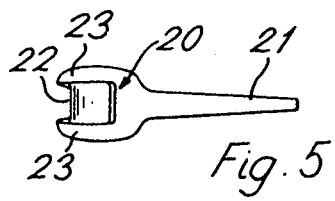
Figure 7:
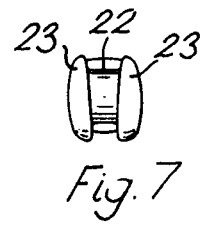
Figure 6:
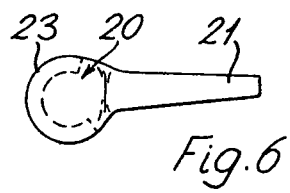

While the ribs 23 are generally parallel, they are not precisely so and, as shown in FIGS. 5 and 7, the groove 22 is progressively widened towards one longitudinal end. As shown by FIG. 6, the groove 22 has end wall portions.

Figure 8:

Also, as shown by FIG. 8, of which the section is taken in a similar plane to that of FIG. 4, the groove 22 has relatively flat side wall portions while the ribs 23 each have a curved radially outer periphery and transversely outermost side. The profile of FIG. 8 is, in fact, generally complementary to that of FIG. 4, but not precisely so in that the rib 13 is narrower than the groove 22 at least at the widened end of the latter.

Turning to the inter-relation of the two illustrated components; it has just been noted that the cross-sectional profiles of the two bearing surfaces are generally complementary, and this allows mutual engagement between the corresponding grooves and ribs providing that the longitudinal extent of the convex groove and ribs exceeds that of the concave grooves and rib, and that the latter subtend an angle not greater than 180°. Given such engagement, the two components have a capability for mutual articulation by sliding in the longitudinal direction of the arcuate formations. The angular range of this sliding will be determined by the extent to which the convex formations exceed the concave formations longitudinally, this range being limited by abutment of the ends of the rib 13 with the end wall portions of the groove 22. This range will normally be at least 90° and in the case of a metacarpophalangeal device will preferably be about 100° – 110° to accord with the flexion-extension range in the normal finger.

Also, in so far as the groove 22 is widened towards one end, the two components have a capability, when engaged with the rib 13 in the wider end portion of the groove 22, for mutual articulation by rocking in the transverse direction. More specifically, the cross-sectional profiles of the bearing surfaces have transversely outermost curved forms which can be subjected to mutual sliding at one side of the engaged device during this secondary articulation but, whether or not this occurs, the groove 12 and rib 13 at the other side of the device separate. The angular range of such articulation is limited by engagement of the side wall portions of the groove 22 with the rib 13. This range will normally be much smaller than that for the longitudinal sliding and in the case of a metacarpophalangeal device will preferably be about 10° – 40° to accord generally with maximum abduction-adduction of about 60°, 45° 45° and 50° in the first to fourth fingers respectively. It is, in any case, to be noted that this secondary articulation capability is only available towards one end of the range of primary articulation corresponding to the widened end of the groove 22, and this accords with progressive decrease of abduction-adduction capability with increasing volar flexion in the normal finger.

This last point leads to another factor in the inter-relation of the above first and second components, namely, that they are respectively adapted for fixation to the relevant metacarpal and proximal phalangeal bones such that the rib 13 is engaged with the wider end, and abutted with the corresponding end wall portion, of the groove 22 when the bones are disposed for zero flexion. In this particular instance such fixation adaption is effected by the provision of elongate members 11 and 21 as intramedullary stems and formation of the respective grooves and ribs at appropriate angular dispositions relative to the longitudinal axes of these members.

A remaining point to note regarding application of the illustrated components to a metacarpophalangeal device is that the rounded bodies 10 and 20 afford a simulated knuckle when engaged, this simulation being enhanced by the earlier-mentioned overhang of the body 10 relative to its rib 13, which overhang is intended to be located in the dorsal aspect and lend continuity between the surfaces of the bodies 10 and 20 in this aspect.

Regarding manufacture of the illustrated embodiments, these are preferably of integral construction from material of suitable biological and mechanical properties. Currently the tendency is to employ a metal such as stainless steel or chromium-cobalt alloy, and a plastics material such as high density polyethylene, for the respective components of an indirectly linked endoprosthetic articulatory bone joint device, and such a choice is clearly a possibility for the present invention. However, the bearing surfaces of the two components involve re-entrant formations which may present difficulty in respect of manufacture from metal. Indeed, in a recently developed modification a first component similar to that of the drawings has the outer side walls of its grooves flattened to facilitate manufacture from metal. This modified first component has been used with a plastics material second component as illustrated and the resultant device has proved stable in use.

An alternative possibility is the use of plastics materials for both components. Such a possibility may not be appropriate to a device subjected to higher order loading in use, but can be adequate in the case of the lower order loading of a finger joint.

Turning lastly to a more general consideration of the invention: the provision of the secondary articulation capability involves a reduction of constraints which might otherwise require undue effort to employ the primary articulation capability. More specifically, the rocking action necessarily involves a freedom for partial separation of the bearing surfaces, and this freedom is not consistent with undue friction or stiffness in the primary sliding action. Also, this freedom suggests the possibility, notwithstanding the above comments on manufacturing difficulty, of manufacture with reduced tolerances compared to other devices of a similar nature.

However, this freedom is not so extensive that the device can be regarded as unstable. The inter-engagement of grooves and ribs serves to track the components during mutual articulation in the sense that the desired articulation cannot be distorted by significant translation movements, and also serves to limit the extent of such articulation.

Also, while the invention has been described with reference to the illustrated embodiment, it is not intended to be limited thereby.

We claim:
1. An endoprosthetic bone joint device, comprising:
a first component including a first rounded body partially recessed to define a first bearing surface consisting of two similar, generally parallel, longitudinally concave, arcuate elongate portions, and a longitudinally concave, arcuate rib laterally separating said portions;
and said first component further including a first stem projecting integrally from said body, remotely from said bearing surface, in the plane of said rib, and in an inclined direction relative to the arcuate bisector of said rib;

and a second component including a second rounded body partially recessed to define a second bearing surface consisting of two similar, generally parallel, longitudinally convex, arcuate ribs, and a longitudinally convex groove laterally separating said convex ribs;

and said second component further including a second stem projecting integrally from said second body, remotely from said second bearing surface, in the plane of said convex groove, and generally parallel to the arcuate bisector of said convex groove;

said first and second bearing surfaces being of generally complementary form in mutual engagement, with said concave rib received in said convex groove, and with said convex ribs received on said concave portions;

said concave portions and rib, and said convex ribs and groove, respectively subtending angles less and greater than 180° to allow longitudinal arcuate sliding between said components;

and said convex groove being widened towards one end thereof to allow lateral rocking between said components.

2. A device according to claim 1 wherein said widened end of said convex groove engages the end of said concave rib further from said first stem.

3. A device according to claim 1 wherein said first body overhangs the end of said concave rib further from said first stem.

4. A device according to claim 1 wherein said convex groove and concave rib have generally rectangular cross-sectional shape, and said concave portions are grooves having a common innermost side wall formed by said concave rib and outermost side walls having laterally concavely curved inner surfaces.

5. A device according to claim 4 wherein said outermost side walls reduce in height towards their longitudinal ends.

6. A device according to claim 4 wherein said components are each of integral, plastics material construction.

7. The use of a device according to claim 1 which comprises respectively implanting said first and second components, by way of said stems, in the metacarpal and proximal phalangeal bones to replace, by said first and second surfaces, the natural articulation surfaces of said bones.

* * * * *